US011529018B2

(12) United States Patent
Barandun et al.

(10) Patent No.: US 11,529,018 B2
(45) Date of Patent: Dec. 20, 2022

(54) METERING APPARATUS

(71) Applicant: FFM PROJEKT AG, Wil (CH)

(72) Inventors: Urs Barandun, Stettfurt (CH); Cyrill Binder, Zürich (CH)

(73) Assignee: FFM Projekt AG, Wil (CH)

( * ) Notice: Subject to any disclaimer, the term of this patent is extended or adjusted under 35 U.S.C. 154(b) by 428 days.

(21) Appl. No.: 16/643,445

(22) PCT Filed: Jul. 13, 2018

(86) PCT No.: PCT/EP2018/069063
§ 371 (c)(1),
(2) Date: Feb. 28, 2020

(87) PCT Pub. No.: WO2019/042646
PCT Pub. Date: Mar. 7, 2019

(65) Prior Publication Data
US 2020/0187714 A1    Jun. 18, 2020

(30) Foreign Application Priority Data

Aug. 29, 2017  (CH) .................................... 01066/17

(51) Int. Cl.
*A47J 37/12* (2006.01)
*A23L 3/36* (2006.01)
(Continued)

(52) U.S. Cl.
CPC ........... *A47J 37/1228* (2013.01); *A23L 3/361* (2013.01); *A23L 3/365* (2013.01); *A47J 37/1214* (2013.01);
(Continued)

(58) Field of Classification Search
CPC ................ A47J 37/1228; A47J 37/1214; A47J 37/1219; A47J 37/1223; A47J 37/1257;
(Continued)

(56) References Cited

U.S. PATENT DOCUMENTS 1,610,564 A * 12/1926 McLaughlin ....... A47J 37/1228
99/407
2,643,021 A *  6/1953 Freedman ............. A47J 41/022
220/592.27
(Continued)

FOREIGN PATENT DOCUMENTS

EP         0636334 A1    2/1995
FR         2672409 A1    8/1992
(Continued)

OTHER PUBLICATIONS

International Search Report and Written Opinion for related PCT App No. PCT/EP2018/069063 dated Oct. 5, 2018, 14 pgs.
(Continued)

*Primary Examiner* — Emmanuel E Duke
(74) *Attorney, Agent, or Firm* — Procopio, Cory, Hargreaves & Savitch LLP

(57) ABSTRACT

A metering apparatus (1) for metering frozen piece goods, comprising a housing (10) which defines a refrigerated chamber (11), wherein a piece goods container (3), a first conveyor unit (4), and a weighing unit (5) are arranged in the refrigerated chamber (11), wherein piece goods can be transported from the piece goods container (3) via the first conveyor unit (4) to the weighing unit (5), wherein an airlock (13) is arranged below the weighing unit (5), through which piece goods can pass out of the refrigerated chamber (11).

20 Claims, 6 Drawing Sheets

(51) Int. Cl.
*A23L 3/365* (2006.01)
*G01K 13/00* (2021.01)
*G01N 33/03* (2006.01)
*G07F 9/10* (2006.01)
*G07F 17/00* (2006.01)
*G01G 13/00* (2006.01)

(52) U.S. Cl.
CPC ........ *A47J 37/1219* (2013.01); *A47J 37/1223* (2013.01); *A47J 37/1257* (2013.01); *A47J 37/1271* (2013.01); *A47J 37/1295* (2013.01); *G01K 13/00* (2013.01); *G01N 33/03* (2013.01); *G07F 9/105* (2013.01); *G07F 17/0085* (2013.01); *A23V 2002/00* (2013.01); *G01G 13/00* (2013.01)

(58) Field of Classification Search
CPC ................ A47J 37/1271; A47J 37/1295; A47J 37/1276; A23L 3/361; A23L 3/365; G01K 13/00; G07F 9/105; G07F 17/0085; G07F 13/025; G07F 17/0078; A23V 2002/00; G01G 13/00; G01G 13/08; F25D 25/00; F25D 13/06

See application file for complete search history.

(56) References Cited

U.S. PATENT DOCUMENTS

| | | | | |
|---|---|---|---|---|
| 3,357,341 | A | * | 12/1967 | Kocken ................ G01G 13/00 99/334 |
| 4,722,267 | A | * | 2/1988 | Galockin ............ G07F 17/0085 126/374.1 |
| 5,003,868 | A | * | 4/1991 | Higgins .............. A47J 37/1228 99/357 |
| 5,163,356 | A | * | 11/1992 | Chigira .................. G07F 9/105 99/286 |
| 5,325,766 | A | * | 7/1994 | Mareels .............. A47J 37/1228 99/357 |
| 5,353,847 | A | * | 10/1994 | Cahlander .............. B65B 37/08 141/168 |
| 5,735,192 | A | * | 4/1998 | Paez .................. G07F 17/0078 99/330 |
| 2003/0218541 | A1 | * | 11/2003 | Sakai ..................... G08B 13/08 340/545.1 |

FOREIGN PATENT DOCUMENTS

FR        2708771 A1 * 2/1995 .......... A47J 37/1228
KR     2005080198 A * 2/2004

OTHER PUBLICATIONS

International Preliminary Report on Patentability for related PCT App No. PCT/EP2018/069063 dated Mar. 12, 2020, 14 pgs.

* cited by examiner

METERING APPARATUS

CROSS-REFERENCE TO RELATED APPLICATIONS

This application is a U.S. National Stage entry of PCT Application No: PCT/EP2018/069063 filed on Jul. 13, 2018, which claims priority to CH Patent Application No. 01066/17, filed Aug. 29, 2017, the contents of which are incorporated herein by reference.

TECHNICAL AREA

The present invention relates to a metering apparatus, in particular for metering frozen piece goods.

PRIOR ART

A metering apparatus for an automatic deep fryer is known from WO 2000/014206, in which during the metering a connection exists between the interior of the metering apparatus and the surroundings, whereby warm ambient air can penetrate into the metering apparatus interior. Since the ambient air is warmer, it contains more moisture, which condenses on the cool structures of the metering apparatus and results in accumulations of ice. In an automatic deep fryer, the air above the frying unit contains water and oil. Both will cause ice or oil, respectively, to accumulate in the interior of the metering apparatus over time.

A metering apparatus is known from WO 2008/124954, which solves the above-described problem in that the metering apparatus is arranged below the frying unit. However, this arrangement requires a complex transportation of the metered piece goods from the metering apparatus to the frying unit.

DESCRIPTION OF THE INVENTION

One object of the present invention is to provide a simple and cost-effective metering apparatus, in which a connection between the metering apparatus interior and the surroundings exists for the shortest possible time.

This object is achieved by a metering apparatus having the features of claim 1. Further embodiments of the metering apparatus, an automatic deep fryer having a metering apparatus according to the invention, and a method for metering frozen piece goods are defined by the features of further claims.

A metering apparatus according to the invention for metering frozen piece goods comprises a housing which defines a refrigerated chamber. A piece goods container, a first conveyor unit, and a weighing unit are arranged in the refrigerated chamber, wherein piece goods are transportable from the piece goods container via the first conveyor unit to the weighing unit. An airlock, through which piece goods can pass out of the refrigerated chamber, is arranged below the weighing unit, for example, vertically below it. This construction is very compact and space-saving and enables very short phases in which the refrigerated chamber is connected to the surroundings and thus prevents excess penetration of ambient air into the refrigerated chamber. The piece goods container can accommodate different piece goods or bulk goods and has a capacity in a range of 40 to 60 liters, for example, 55 liters. The type of the piece goods determines the weight which the piece goods container has to withstand. The piece goods container comprises a sheet-metal construction having a wall thickness of 0.5 to 3 millimeters to be able to withstand weights of 20 to 60 kilograms. For example, frozen piece goods made of meat, fish, vegetables, or baked goods or made of a combination thereof can be stored in the piece goods container before they are metered. Popular frozen piece goods are, for example, French fries, chicken nuggets, spring rolls, falafel, onion rings, fish sticks, shrimp, calamari, doughnuts, or apple rings. A refrigeration module ensures the desired low temperatures in the refrigerated chamber. For example, the refrigeration module comprises a conventional compression refrigeration circuit.

In one embodiment, the housing comprises a jacket having an insulation arranged therein. The jacket has a thickness of less than 1 millimeter up to multiple millimeters, for example, 0.3 to 3 millimeters. The jacket material comprises metal, for example, stainless steel, such as chromium steel, for example, 1.4404 or 1.4301 steel, aluminum, for example, EN AW-5754 or EN-AW-6082, or plastic, for example, ABS or SB. The insulation has a thickness of 10 to 200 millimeters, for example, 100 millimeters. The insulation comprises plastic foam, for example, PU, EPS, EPP foam or VIP vacuum panels or a combination thereof. Such a construction is light, wherein the jacket or the combination of insulation and jacket provides the housing with the required structural stability and the insulation provides the required thermal insulation properties.

In a further embodiment, the jacket partially comprises metal and partially comprises plastic. Different mechanical and thermal behaviors may be implemented by the different materials of the jacket parts. For example, metal has better heat conduction properties than plastic. Heat can be conducted from the housing interior specifically into defined internal regions by a metallic jacket. The heat conduction out of defined regions can be reduced using a plastic jacket.

In a further embodiment, the jacket of the housing comprises metal in the contact region with a slide of the airlock and plastic in a connector region above the slide. The slide comprises an insulating core, for example, made of the above-mentioned materials and a metallic jacket, for example, made of the above-described materials. The ambient heat is conducted by the metallic housing jacket and the metallic slide jacket into the contact region between jacket and slide, whereby the two parts can be prevented from freezing in place. The housing jacket made of plastic in the region above the slide has an insulating effect, whereby the heat is not excessively discharged in the contact region. Optionally, the adjoining region of the slide jacket adjacent to the contact region can also comprise plastic, whereby the dissipation of the heat out of the contact region is further reduced.

In a further embodiment, a tightly closable filling opening is provided in the jacket, in the region above the piece goods container. This simplifies the filling and ensures that heat does not enter the refrigerated chamber through the closed opening. Alternatively, the closable filling opening can also be provided laterally to the piece goods container. The closure can optionally comprise a security element, for example, a lock, whereby the access to the piece goods container is only possible for authorized persons. Conventional seals can be used, as are used, for example, in refrigerators or freezers.

In a further embodiment, the piece goods container is formed funnel-shaped having a delimiting upper opening and having a delimiting lower opening, wherein the upper opening is multiple times larger than the lower opening. This construction facilitates the filling of the piece goods container and permits good pre-metering of the piece goods onto the first conveyor unit located underneath. For example, the lateral surfaces of the piece goods container converge from the upper opening to the lower opening, wherein the lateral surfaces are inclined by different amounts. For example, one, two, or three sides are formed steep and extend nearly vertically, i.e., at an exterior angle of somewhat less than 90 degrees with respect to the horizontal, and one side is formed flat and extends at an exterior angle of 45 degrees or less with respect to the horizontal.

In a further embodiment, the first conveyor unit comprises a first conveyor line and a conveyor drive, wherein the conveyor drive can apply oscillations to the conveyor line in such a way that piece goods located thereon are movable in a predetermined transport direction. The oscillation-based conveyance of the piece goods is reliable, low maintenance, and gently conveys the piece goods. The first conveyor line extends from the lower opening of the piece goods container to the weighing unit and has a length of 300 to 1000 millimeters, for example, 700 millimeters.

In a further embodiment, the first conveyor line is formed inclined with respect to the horizontal. The conveying speed can be increased by the inclination of the conveyor line, whereby the conveying time of piece goods which is required for the conveyance from the piece goods container to the weighing unit is reduced.

In a further embodiment, the first conveyor line converges conically from its side arranged below the piece goods container to its side arranged above the weighing unit, for example, at an angle of 5 to 30 degrees with respect to the longitudinal direction of the conveyor line. Lateral delimitations are provided on the first conveyor line which prevent piece goods from being able to fall down laterally from the conveyor line and deflection elements are provided on the upper side of the conveyor line, using which the piece goods can be deflected transversely to the transportation direction. By way of this construction, the piece goods are reliably isolated and transferred in a bounded, predetermined region to the weighing unit. This permits the use of a space-saving weighing unit. The lateral delimitations are preferably formed continuously and without gaps, whereby piece goods or piece good parts are prevented from being able to fall laterally off of the conveyor line and thus soil the refrigerated chamber. The deflection elements can be formed continuously or having gaps. The gaps are to be dimensioned, however, in such a way that piece goods or piece good parts cannot stick therein. The deflection elements can be formed integrally together with the conveyor line or they can be arranged detachably thereon. In the case of an integral formation, the deflection elements can be aligned optimized for specific piece goods, whereby a piece-goods-optimized conveyor line results. Detachable deflection elements permit an application-specific adaptation of the conveyor line to the piece goods to be conveyed. The deflection elements are aligned at an angle with respect to the general conveying direction, i.e., from the piece goods container to the weighing unit. The angle can be 5 to 60 degrees with respect to the general conveying direction. The deflection elements can extend from a side wall of the conveyor line into the middle of the conveyor line or beyond this in the direction of the opposing side wall.

In a further embodiment, the weighing unit comprises a metering scale and a metering container connected thereto, wherein the weight of the piece goods located in the metering container is measurable using the metering scale. Piece goods are conveyed until a predetermined value of the measured weight is reached. The metering container is formed to be at least partially pivotable, whereby the piece goods located in the metering container are removable therefrom. The metering container can be pivotable as a whole or parts of the metering container can be pivotable. For example, one or two bottom flaps of the metering container can be pivotable. This permits rapid emptying of the metering container which is gentle to the piece goods. In the case of rapid emptying, the required time in which the airlock has to be open is shortened.

In a further embodiment, the weighing unit comprises a counter unit, using which the individual piece goods, which are supplied to the weighing unit before the weighing, can be counted. This is advantageous since certain larger piece goods are not metered according to weight but rather according to piece count. In this case, piece goods are conveyed until a predetermined value of the measured number is reached.

In a further embodiment, the airlock comprises a movable slide, which can release a region of the housing located under the weighing unit. The slide can be formed in one piece or multiple parts. A one-piece slide can be moved in its entirety. In the case of a multipart slide, all parts can be moved simultaneously or the different parts can be moved at least partially offset from one another in time. For example, only a small part of the slide can be moved if small piece goods are to pass the airlock and all parts of the slide can be moved together if large piece goods are to pass the airlock.

In a further embodiment, the airlock can execute at least one movement selected from the group of displacement, pivoting, and folding. For example, the airlock slide can be completely or partially linearly displaced, laterally pivoted away or rotated away, or folded away downward. A construction having a linearly displaceable slide has a low structural height and is simple and low maintenance. The airlock can optionally comprise guide rails, which are designed in such a way that the slide or slide parts guided therein are moved toward the housing in the last rail section before the closing of the housing, whereby a better seal can be implemented. For example, the guide rails can describe curved paths, which are inclined with respect to the adjoining housing wall in the closing range, i.e., in the last rail section, with respect to the adjoining housing wall and which are otherwise formed in parallel to the adjoining housing wall. Alternatively, the guide rails can be formed linear and can be formed at an angle with respect to the adjoining housing wall.

In a further embodiment, the metering apparatus comprises a refrigerated chamber fan, which can aspirate outside air from outside the metering apparatus to be able to generate an overpressure in the refrigerated chamber. It is thus possible to prevent ambient air from penetrating through the airlock into the refrigerated chamber when the airlock is open and water or oil contained in the ambient air from precipitating in the refrigerated chamber. The outside air which can be supplied through the refrigerated chamber fan to the refrigerated chamber is generally oil-free. To withdraw the contained moisture from the outside air, a drying unit can optionally be provided, which can be arranged before or after the refrigerated chamber fan. The refrigerated chamber fan can be arranged anywhere in the refrigerated chamber, for example, in the region of the airlock. Partition walls which adjoin the region of the airlock opening additionally prevent a free air exchange between the airlock region and the refrigerated chamber and thus prevent the heat exchange between the ambient air and the refrigerated chamber when the airlock is open. The partition walls can partially or completely enclose the airlock opening. The partition walls can at least partially accommodate the metering container. The partition walls can adjoin the metering container approximately leak-tight, whereby the passage between the refrigerated chamber and the surroundings is nearly completely closed by the metering container when the airlock is open.

In a further embodiment, the metering apparatus comprises one or more heating modules, which are arranged in the refrigerated chamber and designed in such a way that they can thaw and/or liquefy accumulations of ice and/or oil in the refrigerated chamber. Water and/or oil which has precipitated in the refrigerated chamber can thus be at least partially removed from the refrigerated chamber again, whereby a growth of the deposits can be prevented. An apparatus failure because of ice or oil accumulation can thus be avoided. For example, a heating module can be arranged in the region of the filling opening, in the region of the metering container and/or the airlock, in the region of a heat exchanger, or in the region of the refrigerated chamber fan.

An automatic deep fryer according to the invention for frying frozen piece goods comprises a housing, a metering apparatus according to the invention, which is arranged in the upper region of the housing, a frying unit, which is arranged in the housing below the metering apparatus, wherein piece goods which leave the metering apparatus through the airlock can reach the frying unit. This is a simple construction and offers a direct and short connection between the airlock of the metering apparatus and the frying unit.

In a further embodiment, the automatic deep fryer comprises a second conveyor unit, using which piece goods which can be transported to the frying unit. By way of this arrangement, the frying unit is not located directly below the airlock, whereby rising water or oil particles cannot directly reach the airlock or the refrigerated chamber of the metering apparatus.

In a further embodiment, the automatic deep fryer comprises an airlock fan, which is designed in such a way that rising vapors of the frying unit can be kept away from the airlock. The refrigerated chamber of the metering apparatus is thus additionally protected from vapors or fumes which can contain water and oil.

In a further embodiment of the automatic deep fryer, two or more metering apparatuses for storing and metering different piece goods are arranged adjacent to one another in the automatic deep fryer housing, wherein two or more conveyor units can be provided, which can transport the respective piece goods from the metering apparatuses to a common frying unit or which can transport the respective piece goods to a frying unit provided separately for them. Such a construction permits the essentially simultaneous preparation of different piece goods. For example, French fries and chicken nuggets can be prepared simultaneously or can be prepared offset in time depending on the required cooking time, so that the end of cooking occurs simultaneously and they are removable together from the automatic deep fryer.

In a further embodiment, the automatic deep fryer comprises a third conveyor unit, using which the fried piece goods can be transported to a removal unit. Furthermore, the automatic machine comprises an input unit, at which a user can select the product or the products which he wishes to have prepared. At a payment unit, the user can pay for the product selected by him using conventional means. A security unit triggers an alarm if the automatic machine is damaged, if an attempt is made to break into the automatic machine, if an attempt is made to transport the automatic machine without authorization, or if the automatic machine is raised or tilted. A transmission unit can transmit data wirelessly or by means of a cable connection from an automatic machine to a central office. This can be performed by means of conventional wireless or wired transmission technologies. For example, a triggered alarm can thus be transmitted to the central office. The fill level in the piece goods containers by means of a corresponding fill level measurement or the fill level of the oil in the frying unit or the temperature in the refrigerated chamber or of the oil can also be transmitted. Data for the payment can additionally be transmitted to the central office or retrieved therefrom.

A method according to the invention for metering frozen piece goods comprises the following steps:
providing a metering apparatus according to the invention;
filling the piece goods container with frozen piece goods;
conveying the frozen piece goods from the piece goods container to the weighing unit using the first conveyor unit;
weighing the piece goods;
opening the airlock;
emptying the weighed piece goods through the open airlock; and
closing the airlock.

Using such a method it is possible to prevent ambient air, which can contain water and oil, from penetrating into the refrigerated chamber of the metering apparatus and precipitating therein.

The mentioned embodiments of the metering apparatus, the automatic deep fryer, and the metering method may be used in any arbitrary combination if they do not contradict one another.

BRIEF DESCRIPTION OF THE FIGURES

Exemplary embodiments of the present invention are explained in greater detail hereafter on the basis of figures. They only serve for explanation and are not to be interpreted as restrictive. In the figures.

DETAILED DESCRIPTION OF THE INVENTION

Figure 1:
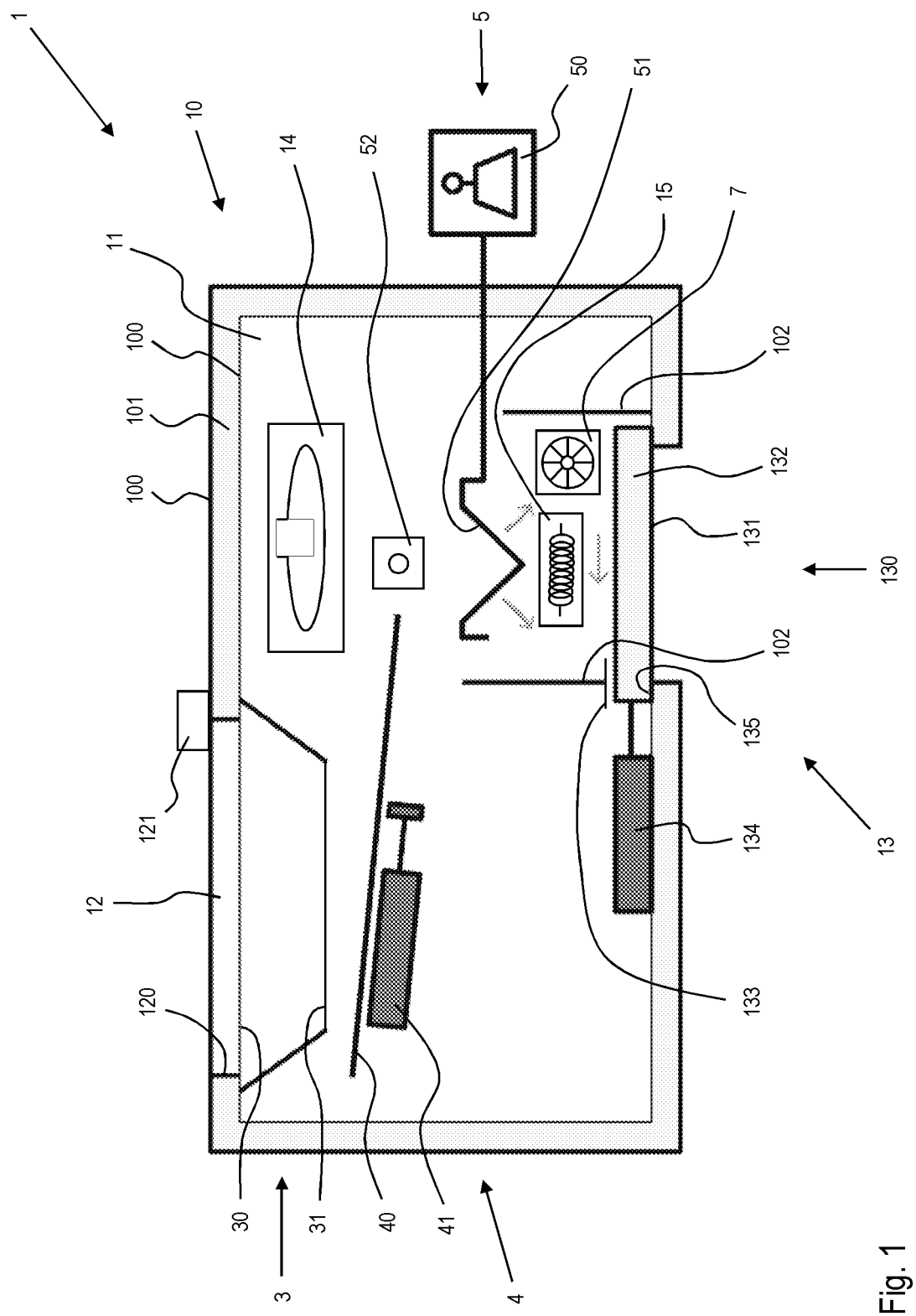
FIG. 1 shows a schematic sectional view of a metering apparatus according to the invention.

FIG. 1 shows a schematic sectional view of a metering apparatus 1 according to the invention. The metering apparatus 1 comprises a housing 10, which delimits a refrigerated chamber 11. The housing 10 comprises a jacket 100, which essentially completely internally and/or externally encloses an insulation core 101. A funnel-shaped piece goods container 3 having an upper opening 30 and a lower opening 31 is provided in the refrigerated chamber 11, wherein the upper opening 30 is multiple times larger than the lower opening 31. A first conveyor unit 4 having a first conveyor line 40 and a conveyor drive 41 is provided below the piece goods container 3, using which piece goods can be transported from the piece goods container 3 to a weighing unit 5, which is arranged laterally below the lower opening 31 of the piece goods container 3. The weighing unit 5 comprises a metering scale 50, using which the weight of the piece goods located in a metering container 51 is determinable. A counter unit 52 is provided in the region above the metering container 51, using which the number of the piece goods can be counted which move from the conveyor unit 4 into the metering container 51. An airlock 13 is provided, using which the region of the housing 10 below the metering container 51 can be opened and closed leak-tight again. The airlock 13 comprises a plate-shaped slide 130 having a jacket 131, which essentially completely encloses an insulation core 132. The slide 130 is guided in guides 133 arranged on the housing 10 and can be laterally displaced using an actuator 134. The displacement occurs essentially in parallel to the housing bottom, on which the slide 130 is arranged. To improve the seal of the refrigerated chamber 11 in relation to the surroundings, seals 135 are provided in the contact region of the slide 130 with the housing 10. A refrigeration module 14 ensures the required low temperatures in the refrigerated chamber 11. A heating module 15 arranged in the region of the airlock 13 can thaw accumulations of ice in this region. Partition walls 102, which are arranged adjoining the region of the airlock 13 on the interior of the housing 10 and protrude from the housing 10 into the refrigerated chamber 11, prevent the inflow of ambient air into the refrigerated chamber 11 when airlock 13 is open. The partition walls 102 enclose the metering container 51 in such a way that the passage between the refrigerated chamber 11 and the surroundings is closed nearly leak-tight by the metering container 51 when airlock 13 is open. A refrigerated chamber fan 7 is arranged in the region of the airlock 13, using which an overpressure can be generated in the refrigerated chamber 11 using outside air, whereby the penetration of ambient air into the refrigerated chamber 11 through the airlock opening when the airlock 13 is open can be prevented. A tightly closable filling opening 12 is provided in the region above the piece goods container 3 in the housing 10, through which the piece goods container 3 is fillable. Seals 120 are provided in the contact region between the housing 10 and the filling opening 12. The filling opening 12 is closable solidly, tightly, and securely using a closure 121.

Figure 2:
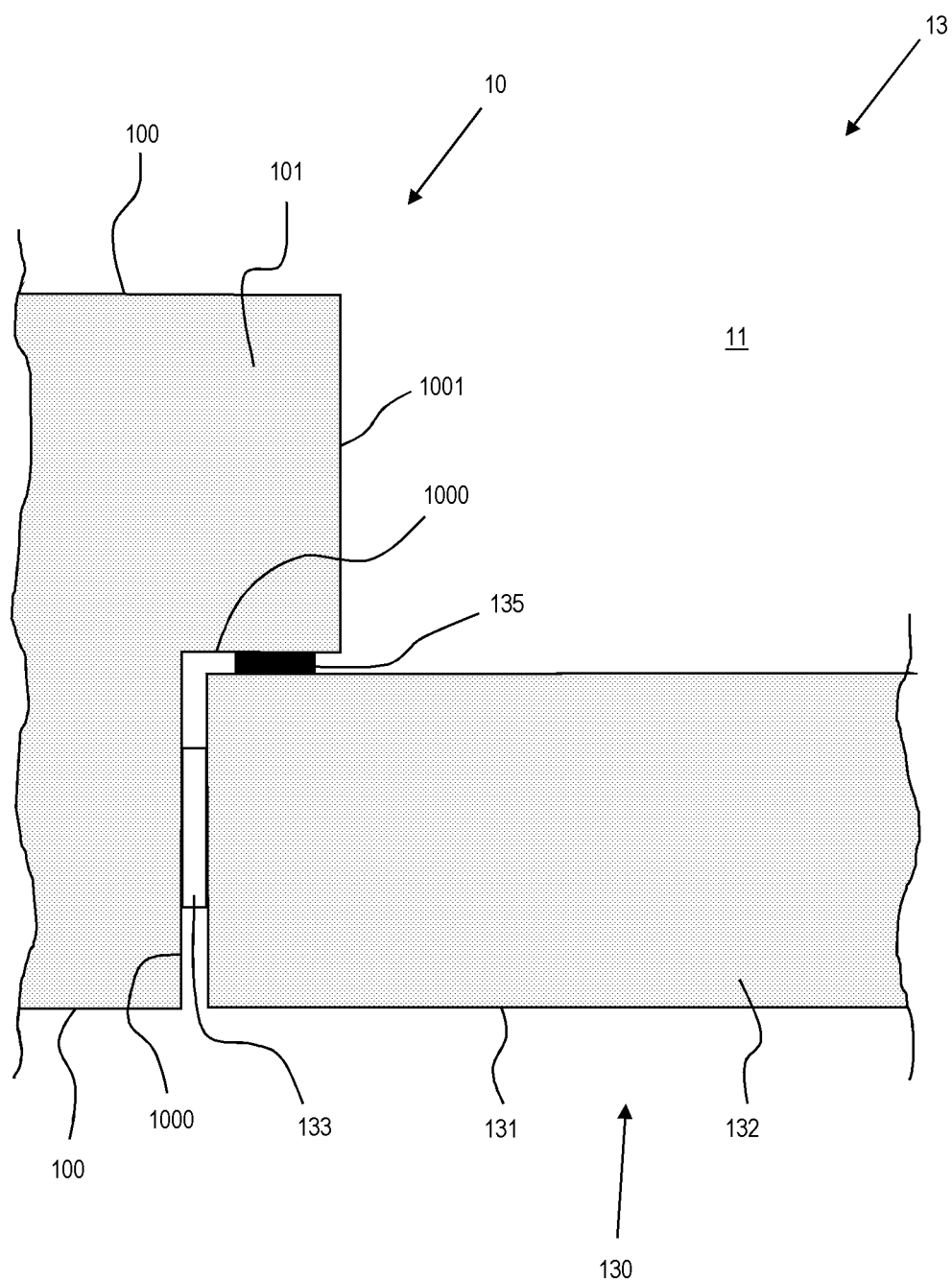
FIG. 2 shows a schematic partial sectional view through the housing and the airlock of FIG. 1.

FIG. 2 shows a schematic partial sectional view through the housing 10 or the housing bottom, respectively, and the airlock 13 of FIG. 1. The housing bottom has an attachment, in which the airlock slide 130 is incorporated essentially aligned with the housing exterior. The slide 130 is guided by guides 133 laterally arranged on the housing 10 in the attachment. A seal 135 is provided on the outwardly oriented face of the attachment and/or on the inwardly oriented face of the slide 130. The slide 130 comprises a chromium steel jacket 131, which essentially completely encloses a plastic insulation core 132. The housing 10 comprises a chromium steel jacket 100, which essentially completely encloses a plastic insulation core 101. In the slide region, the jacket of the housing 10 comprises a contact region 1000 made of chromium steel in the attachment and an attachment region 1001 made of plastic above the attachment.

Figure 3:
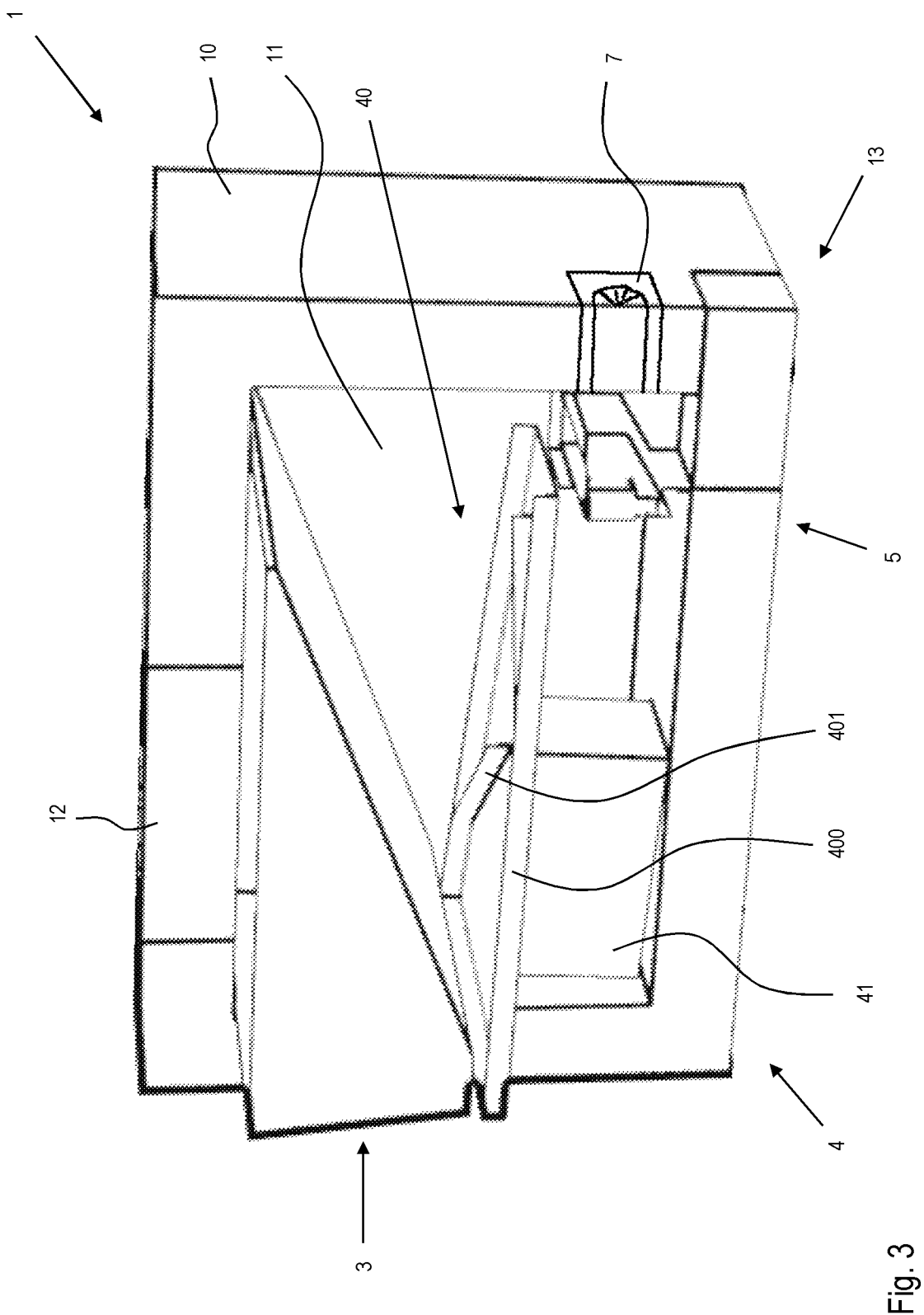
FIG. 3 shows a schematic perspective partial sectional view of the metering apparatus of FIG. 1.

FIG. 3 shows a schematic perspective partial sectional view of the metering apparatus of FIG. 1. The first conveyor line 40 arranged on the conveyor drive 41 tapers conically from its one end located below the piece goods container 3 to its other end located above the weighing unit 5. Lateral delimitations 400 are provided along the tapering section and at the end below the piece goods container 3. Deflection elements 401 extend from the lateral delimitations 400 diagonally in the conveying direction toward the center of the first conveyor line 40 and beyond it. The deflection elements 401 are aligned at an angle with respect to the general conveying direction. For example, at an angle of 30 degrees with respect to the connecting line of the piece goods container 3 to the weighing unit 5.

Figure 4:
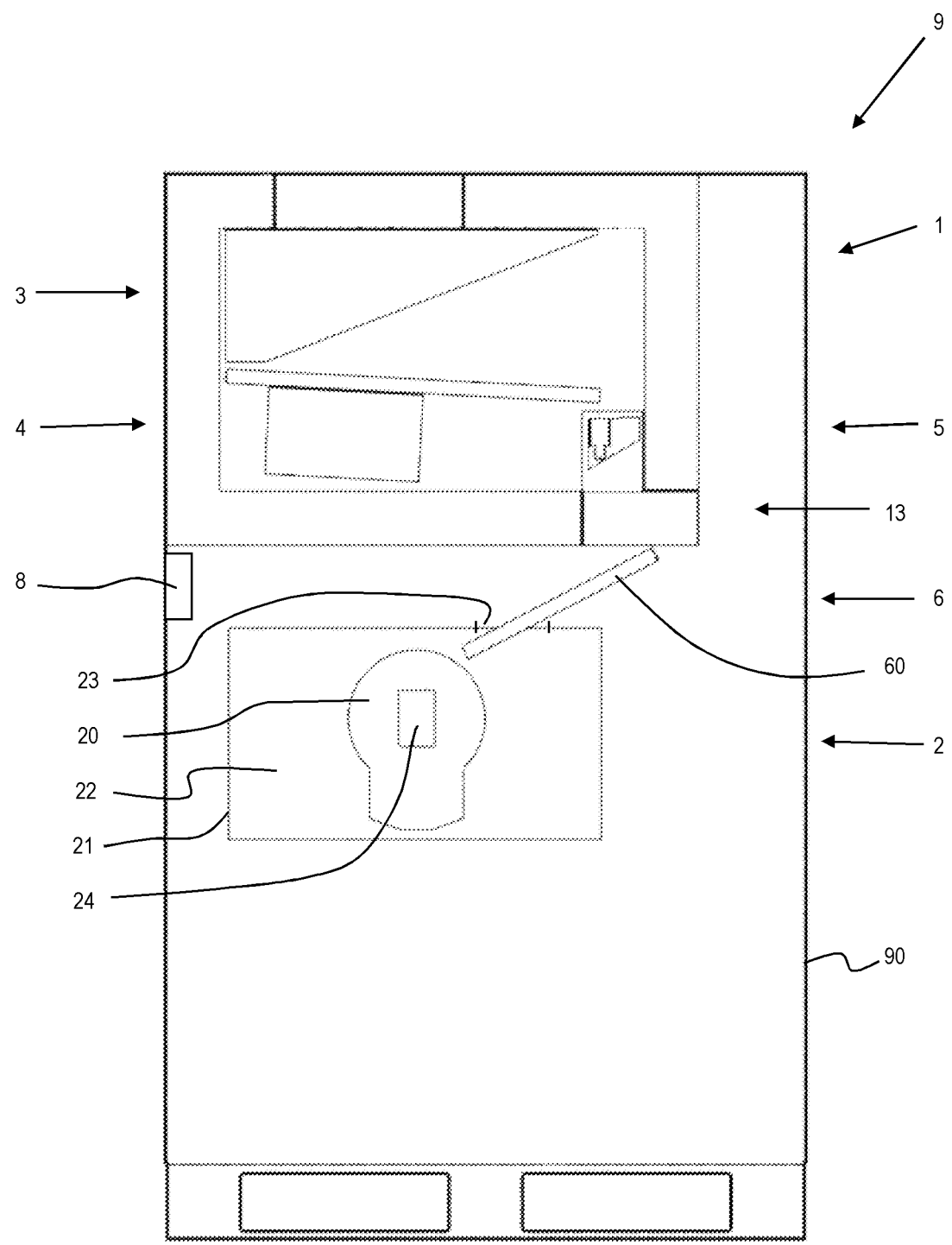
FIG. 4 shows a schematic sectional view of an automatic deep fryer according to the invention.

FIG. 4 shows a schematic sectional view of an automatic deep fryer 9 according to the invention. The automatic deep fryer 9 comprises a closable housing 90 in which a metering apparatus 1 according to the invention and a frying unit 2 are arranged. The metering apparatus 1 is arranged in the upper region of the housing 90 adjoining thereon and the frying unit 2 is arranged below the metering apparatus 1. The frying unit 2 comprises a deep fryer 20, a housing 21, which delimits a frying chamber 22 and comprises an upper inlet opening 23 and a frontal outlet opening 24. The inlet opening 23 of the frying unit 2 is arranged laterally offset to the airlock 13 of the metering apparatus 1. A second conveyor unit 6 having a second conveyor line 60 is arranged between the airlock 13 and the frying unit 2 and extends from the region below the airlock 13 through the inlet opening 23 up to the deep fryer 20. An airlock fan 8 is arranged in the region between the metering apparatus 1 and the frying unit 2 and prevents air rising from the frying unit 2 from reaching the airlock 13.

Figure 5:
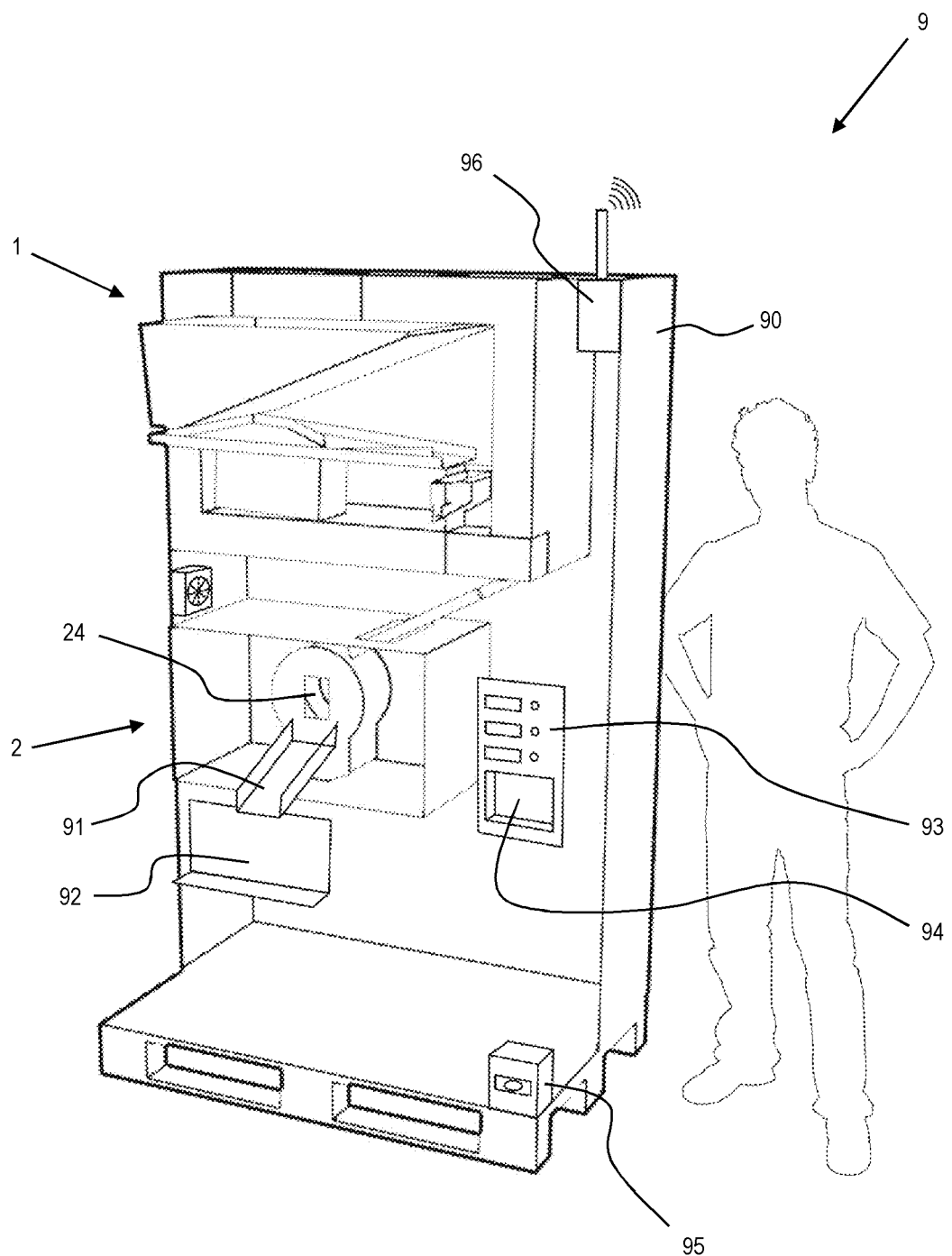
FIG. 5 shows a schematic perspective partial sectional view of the automatic deep fryer of FIG. 4.

FIG. 5 shows a schematic perspective partial sectional view of the automatic deep fryer 9 of FIG. 4. The automatic deep fryer 9 comprises a third conveyor unit 91, which is arranged in the housing 90 and adjoins the outlet opening 24 of the frying unit 2, and a removal unit 92 adjoining thereon. An input unit 93 and a payment unit 94 are arranged on the housing exterior in a region well accessible to a user. A security unit 95 and a transmission unit 96 are arranged in the housing interior.

Figure 6:
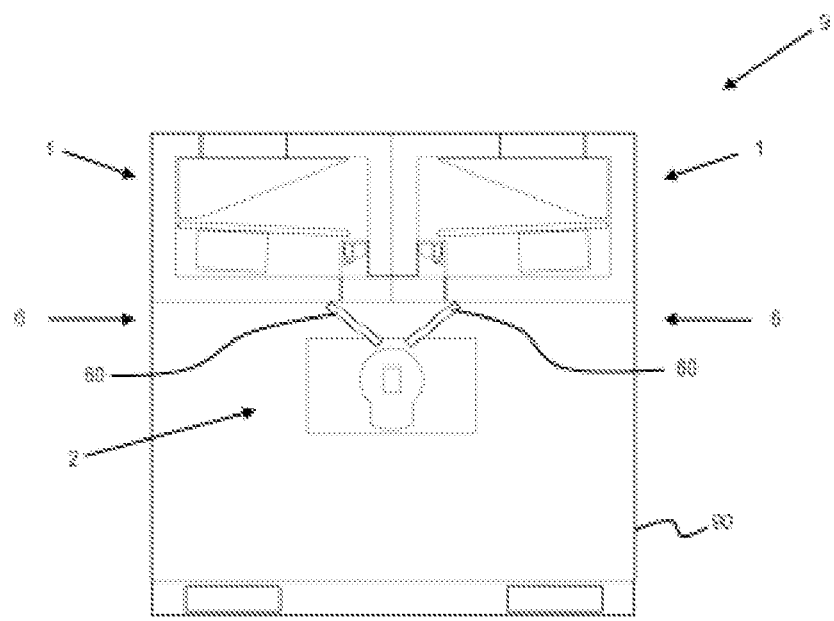
FIG. 6 shows a metering apparatus according to a further embodiment of the invention with two conveyor units that feed a common frying unit.
Figure 7:
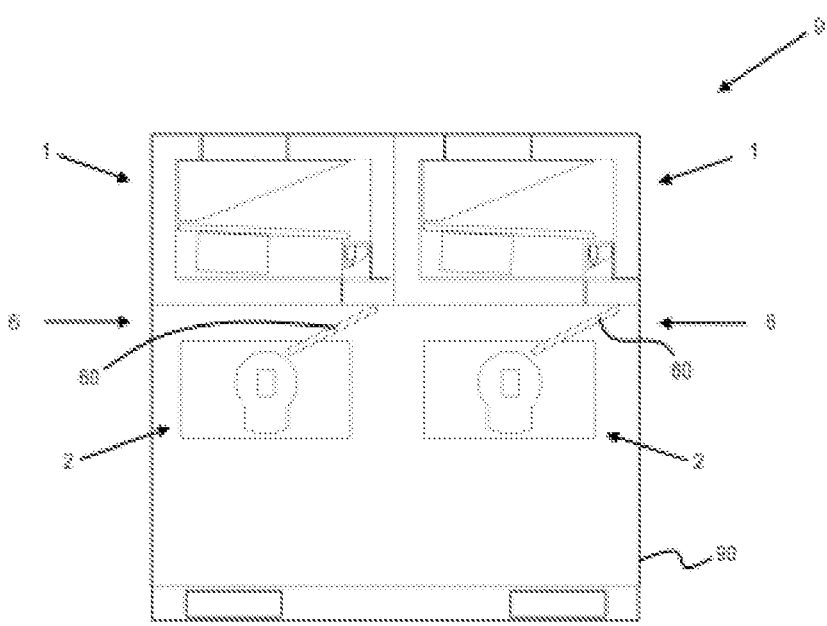
FIG. 7 shows a metering apparatus according to a further embodiment of the invention with two conveyor units that feed separate frying units.

FIG. 6 shows a metering apparatus according to a further embodiment of the invention with two conveyor units 6 that feed a common frying unit 2; and FIG. 7 shows a metering apparatus according to a further embodiment of the invention with two conveyor units 6 that feed separate frying units 2.

LIST OF REFERENCE NUMERALS 1 metering apparatus
10 housing
100 jacket
1000 contact region
1001 connector region
101 insulation
102 partition wall
11 refrigerated chamber
12 filling opening
120 seal
121 closure
13 airlock
130 slide
131 jacket
132 insulation
133 guide
134 actuator
135 seal 14 refrigeration module
15 heating module
2 frying unit
20 deep fryer
21 housing
22 frying chamber
23 inlet opening
24 outlet opening
3 piece goods container
30 upper opening
31 lower opening
4 first conveyor unit
40 first conveyor line
400 lateral delimitation
401 deflection elements
41 conveyor drive
5 weighing unit
50 metering scale
51 metering container
52 counter unit
6 second conveyor unit
60 second conveyor line
7 refrigerated chamber fan
8 airlock fan
9 automatic deep fryer
90 housing
91 third conveyor unit
92 removal unit
93 input unit
94 payment unit
95 security unit
96 transmission unit

The invention claimed is:

1. A metering apparatus for metering frozen piece goods, the metering apparatus comprising: a housing which defines a refrigerated chamber, a piece goods container, a first conveyor unit, and a weighing unit are arranged in the refrigerated chamber, wherein piece goods is configured to be transported from the piece goods container via the first conveyor unit to the weighing unit, wherein an airlock is arranged in a line of fall below the weighing unit, through which piece goods can pass out of the refrigerated chamber wherein the first conveyor unit is a vibratory conveyor and comprises a first conveyor line and a conveyor drive, and wherein the conveyor drive applies oscillations to the first conveyor line so that the piece goods located thereon are moved in a predetermined transportation direction.

2. The metering apparatus according to claim 1, wherein the housing comprises a jacket having an insulation arranged therein.

3. The metering apparatus according to claim 2, wherein the jacket partially comprises a metal and partially comprises a plastic.

4. The metering apparatus according to claim 2, wherein the jacket comprises a metal in a contact region with a slide of the airlock and comprises a plastic in a region above the slide.

5. The metering apparatus according to claim 1, wherein a closable filling opening is provided in the housing, in a region above the piece goods container.

6. The metering apparatus according to claim 1, wherein the piece goods container formed funnel-shaped having a delimiting upper opening and having a delimiting lower opening, and wherein the upper opening is multiple times larger than the lower opening.

7. The metering apparatus according to claim 1, wherein the first conveyor line is formed inclined with respect to horizontal.

8. The metering apparatus according to claim 1 wherein the first conveyor line converges conically from a side of the first conveyor line arranged below the piece goods container to a side of the first conveyor line arranged above the weighing unit, wherein lateral delimitations are provided, which prevent piece goods from being able to fall laterally off of the conveyor line and wherein deflection elements are provided on an upper side of the conveyor line; using which the piece goods are configured to be deflected transversely to the transportation direction.

9. The metering apparatus according to claim 1, wherein the weighing unit comprises a metering scale and a metering container connected thereto,
wherein weight of the piece goods located in the metering container is measurable using the metering scale, and
wherein the metering container is formed to be at least partially pivotable, whereby the piece goods located in the metering container are removable therefrom.

10. The metering apparatus according to claim 1, wherein the weighing unit comprises a counter unit using which individual piece goods are configured to be counted, which are supplied to the weighing unit before the weighing.

11. The metering apparatus according to claim 1, wherein the airlock comprises a movable slide which is configured to release a region of the housing located below the weighing unit.

12. The metering apparatus according to claim 11, wherein the airlock is configured to execute at least one movement selected from a group of displacement, pivoting, and folding.

13. The metering apparatus according to claim 1, further comprising a refrigerated chamber fan which is configured to aspirate air from outside the metering apparatus to be able to generate an overpressure in the refrigerated chamber when the airlock is open.

14. The metering apparatus according to claim 1, further comprising a heating module which is arranged in the refrigerated chamber and configured to thaw accumulations of ice and/or oil in the refrigerated chamber.

15. An automatic deep fryer, comprising: a housing: the metering apparatus according to claim 1, which is arranged in an upper region of the housing; and a frying unit which is arranged in the housing below the metering apparatus, wherein the piece goods which leave the metering apparatus through the airlock is configured to reach the frying unit.

16. The automatic deep fryer according to claim 15, further comprising a second conveyor unit, using which piece goods, which leave the metering apparatus through the airlock, is configured to be transported to the frying unit.

17. The automatic deep fryer according to claim 16, further comprising a third conveyor unit; a removal unit; an input unit; a payment unit; a security unit; and a transmission unit.

18. The automatic deep fryer according to claim 15, further comprising an airlock fan, which is designed in such a way that rising vapors of the frying unit are configured to be kept away from the airlock.

19. The automatic deep fryer according to claim 15, wherein two or more metering apparatuses for storing and metering different piece goods are arranged adjacent to one another in the housing,
wherein two or more conveyor units are provided, which are configured to transport the respective piece goods from the metering apparatuses to a common frying unit or which are configured to transport the respective piece goods to a frying unit provided separately for them.

20. A method for metering frozen piece goods, the method comprising: providing the metering apparatus according to claim 1; filling the piece goods container with frozen piece goods; conveying the frozen piece goods from the piece goods container to the weighing unit using the first conveyor unit; weighing the piece goods; opening the airlock; emptying the weighed piece goods through the open airlock; and closing the airlock.

* * * * *